United States Patent [19]

Koltkamp, Sr.

[11] Patent Number: Plant 6,535

[45] Date of Patent: Jan. 17, 1989

[54] AFRICAN VIOLET PLANT NAMED LOS ANGELES

[75] Inventor: Reinhold Koltkamp, Sr., Isselburg, Fed. Rep. of Germany

[73] Assignee: Gessellschaftsvertrag uber die Erfindergemeinschaft "Optimara", Rees Haffen, Fed. Rep. of Germany

[21] Appl. No.: 56,415

[22] Filed: Jun. 1, 1987

[51] Int. Cl.[4] ..... A01H 5/00

[52] U.S. Cl. ..... Plt./69

[58] Field of Search ..... Plt./69

*Primary Examiner*—James R. Feyrer

*Attorney, Agent, or Firm*—Foley & Lardner, Schwartz, Jeffery, Schwaab, Mack, Blumenthal & Evans

[57] ABSTRACT

An African violet plant named Los Angeles, characterized by its deep blue, semi-double flowers; tight bouquet of flowers on strong peduncles standing free above medium green, strongly serrated girl-type leaves with bright light green centers; vigorous growth habit; and long lasting and non-dropping flowering habit.

1 Drawing Sheet

The present invention comprises a new and distinct cultivar of African violet plant, botanically known as *Saintpaulia ionantha,* and hereinafter referred to by the cultivar name Los angeles.

The new cultivar was referred to during the breeding and selection process by the designation F39/7, and is a product of a planned breeding program. The new cultivar was originated from a cross made by applicant in a controlled breeding program in Haffen, Federal Republic of Germany. The female, or seed parent was a cultivar designated B292. The male, or pollen parent was a cultivar designated 63, named Colorado, and disclosed in U.S. Plant Pat. No. 4,266.

Los Angeles was discovered and selected by me as a flowering plant within the progeny of the stated cross in a controlled environment in Haffen, Federal Republic of Germany. Asexual reproduction of the new cultivar by leaf cuttings, as performed by me at Haffen, Federal Republic of Germany, has demonstrated that the combination of characteristics as herein disclosed for the new cultivar are firmly fixed and retained through successive generations of asexual reproduction.

Los Angeles has not been observed under all possible environmental conditions. The phenotype may vary significantly with variations in environment such as temperature, light intensity and day length. The following observations, measurements and values describe the new cultivar as grown in 10 cm pots in Haffen, Federal Republic of Germany and Nashville, Tenn. under greenhouse conditions which closely approximate those generally used in commercial practice.

The following traits have been repeatedly observed and are determined to be basic characteristics of Los Angeles which in combination distinguish this African violet as a new and distinct cultivar:

1. Strong upright flower stems curving toward the center.
2. Each plant carries 8–9 and more upright flower stems, each of which carries 8 to 11 flowers.
3. Profuse flowering.
4. Seed capsules push slightly through.
5. Vigorous grower.
6. Plant saleable 9–10 weeks after potting.
7. Long-lasting, non-dropping, semi-double deep-blue flowers.

8. Very attractive girl-type leaf, strongly serrated, wavy, curled up at base, with white to light green center.
9. After maturity, the flowers dry off and remain on the peduncle without becoming infected by botrytis.

In comparison to the closest known variety, which is Houston, the similarities are the girl-type leaves and the deep blue color of the flowers. Los Angeles and Houston differ primarily in the number of petals per flower, with Los Angeles being semi-double with five petals, and an additional 6–7 petals of different sizes.

The accompanying color photographic drawing shows a typical specimen plant of the new cultivar. The colors appearing in the photograph are as true as possible with color illustrations of this type.

In the following description, color references are made to the Royal Horticultural Society Colour Chart (RHS), except where general colors of ordinary significance are referred to. Color values were taken under natural light conditions at approximately 2:00 p.m. in Nashville, Tenn.

Botanical classification: *Saintpaulia ionantha,* Ramat., cv. Los Angeles.

Parentage:

*Male parent.*—63, named Colorado.

*Female parent.*—B292.

Propagation: The new cultivar holds its distinguishing characteristics through successive propagations by leaf cuttings and by division of shoots.

Plant: From 7 to 9 cm tall when grown in pots, and approximately 18–20 cm in diameter when fully grown. The growth rate is vigorous.

*Leaves.*—Shape: Round, girl-type, strongly serrated, wavy, hairy, bright light green center radiating along the veins. Diameter: 65 to 80 mm. Texture: Velvety and shiny. Ribs and Veins: Upperside visible, light green toward the center; underside very well pronounced, light green and shiny, with purplish red touch, especially on the younger leaves. Color (upper side): Green 136A. Color (under side): Grayed green, 191 between B and C. Petioles: Strong, upright, light green, purplish red especially on side facing the flowers, hairy.

*Flowers.*—Buds: Purple blue, ball-shaped, 8–9 mm before opening. Sepals: Five (5) in number, purplish brown. Calyx: Funnel-shaped. Aspect: Spear-shaped, hairy. Peduncle: Strong, upright, purplish brown, hairy.

*Individual flowers.*—Size: 30 to 35 mm in diameter. Shape: Semi-double; 3 large and 2 smaller petals plus 6–7 additional petals of different sizes. Color (upper side): Violet blue 89A; under cooler conditions and more intensive lighting, the blue color is more intense. Color (under side): Violet blue 89B-C. Borne: Each flower stem carries 8–11 and more flowers on strong, upright peduncles that are free standing above the leaves and that are curving toward the center of the plant. Flowering habit: Flowers 9–10 weeks after potting; flowering profuse. Corolla: Compact flower head, free-standing abaove the leaves.

*Reproductive organs.*—Stamens: Two (2) in number. Anthers: Two, composed of 4 cells. Filaments: 3 mm long, light green with blue traces. Pollen Color: Yellow 7A. Styles: 6 mm, purplish blue, base of ovary light green and hairy.

*Roots.*—Normally developed, white, turning slightly brownish when older.

Disease resistance: Good.

General observations: Los Angeles is very attractive due to its deep blue semi-double flowers that appear round and full. The anthers are sometimes almost covered up by the many petals. A tight bouquet of flowers on strong peduncles stands free above medium green, strongly serrated girl-type leaves with bright light green center. The flowers are long-lasting and non-dropping.

I claim:

1. A new and distinct cultivar of African violet named Los Angeles, as described and illustrated, and particularly characterized by its deep blue, semi-double flowers; tight bouquet of flowers on strong peduncles standing free above medium green, strongly girl-type leaves with bright light green centers; vigorous growth habit; and long lasting and non-dropping flowering habit.

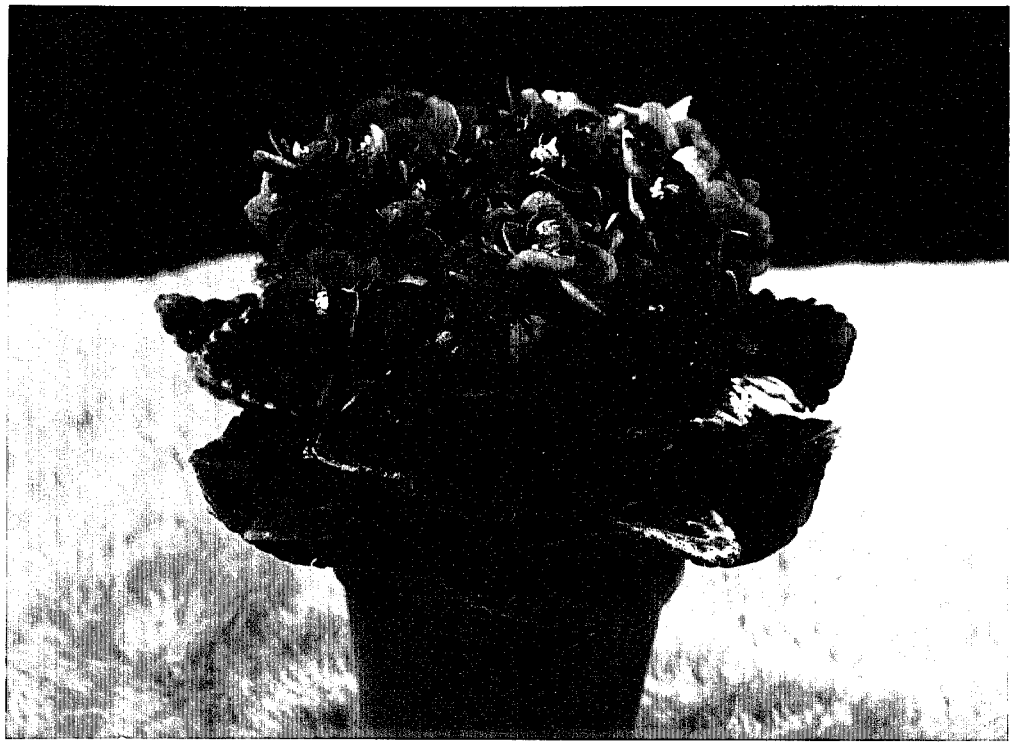

* * * * *